United States Patent
Fabian, Jr.

(10) Patent No.: US 11,253,371 B2
(45) Date of Patent: Feb. 22, 2022

(54) VERTEBRAL BODY SHAVER ASSEMBLY

(71) Applicant: Henry F. Fabian, Jr., Steamboat Springs, CO (US)

(72) Inventor: Henry F. Fabian, Jr., Steamboat Springs, CO (US)

(*) Notice: Subject to any disclaimer, the term of this patent is extended or adjusted under 35 U.S.C. 154(b) by 0 days.

(21) Appl. No.: 17/132,666

(22) Filed: Dec. 23, 2020

(65) Prior Publication Data
US 2021/0220146 A1    Jul. 22, 2021

Related U.S. Application Data

(60) Provisional application No. 62/954,141, filed on Dec. 27, 2019.

(51) Int. Cl.
*A61F 2/44* (2006.01)
*A61B 17/16* (2006.01)
*A61F 2/46* (2006.01)

(52) U.S. Cl.
CPC ........ *A61F 2/4425* (2013.01); *A61B 17/1659* (2013.01); *A61F 2/4611* (2013.01); *A61F 2002/443* (2013.01)

(58) Field of Classification Search
CPC ...... A61F 2/4425; A61F 2/443; A61F 2/4611; A61B 17/1659
See application file for complete search history.

(56) References Cited

U.S. PATENT DOCUMENTS

| | | | |
|---|---|---|---|
| 5,592,727 A | 1/1997 | Glowa et al. | |
| 5,681,337 A * | 10/1997 | Bray Jr. ............. | A61B 17/1611 606/170 |
| 5,733,298 A | 3/1998 | Berman et al. | |
| 6,083,228 A | 7/2000 | Michelson | |
| 6,692,501 B2 | 2/2004 | Michelson | |
| 8,088,135 B2 | 1/2012 | Heisler | |
| 8,465,490 B1 | 6/2013 | White et al. | |
| 9,265,521 B2 | 2/2016 | To et al. | |
| 9,839,441 B2 | 12/2017 | Hayes et al. | |
| 10,321,929 B2 | 6/2019 | Willhite et al. | |
| 2003/0083664 A1 * | 5/2003 | Rogers ............... | A61B 17/1671 606/79 |
| 2005/0240193 A1 * | 10/2005 | Layne .............. | A61B 17/22031 606/80 |
| 2006/0264957 A1 | 11/2006 | Cragg et al. | |
| 2007/0060935 A1 | 3/2007 | Schwardt et al. | |
| 2007/0073398 A1 * | 3/2007 | Fabian .................... | A61F 2/442 623/17.11 |
| 2007/0233130 A1 * | 10/2007 | Suddaby ............ | A61B 17/1659 606/79 |

(Continued)

*Primary Examiner* — Nicholas J Plionis
(74) *Attorney, Agent, or Firm* — Timothy D. Bennett; Emerson Thomson Bennett, LLC

(57) ABSTRACT

A vertebral body shaver assembly may include a shaver inserter and a shaver instrument. The shaver inserter may be used to insert the shaver instrument into an intradiscal space between vertebral body endplates in a non-expanded condition with a footprint area A1. The shaver instrument may then be adjusted into a to an expanded condition with a footprint area A2 that is greater than footprint area A1. As the shaver instrument is adjusted into the expanded condition, at least one blade may shave osteochondral material off at least one of the first vertebral body endplates.

20 Claims, 15 Drawing Sheets

(56) References Cited

U.S. PATENT DOCUMENTS

| | | | |
|---|---|---|---|
| 2008/0021487 A1* | 1/2008 | Heisler | A61B 17/32002 606/170 |
| 2008/0221505 A1* | 9/2008 | Betts | A61B 17/8825 604/22 |
| 2009/0054898 A1* | 2/2009 | Gleason | A61B 17/320725 606/79 |
| 2009/0270873 A1* | 10/2009 | Fabian | A61F 2/4425 606/99 |
| 2010/0010525 A1 | 1/2010 | Lockard et al. | |
| 2010/0121153 A1 | 5/2010 | To | |
| 2011/0319898 A1* | 12/2011 | O'Neil | A61F 2/4425 606/84 |
| 2013/0018376 A1* | 1/2013 | Yoon | A61B 17/320725 606/79 |
| 2013/0060272 A1* | 3/2013 | Thistle | A61B 17/32002 606/170 |
| 2013/0304070 A1* | 11/2013 | Nelson | A61B 17/1659 606/85 |
| 2014/0276834 A1* | 9/2014 | Livorsi | A61B 17/16 606/79 |
| 2021/0212712 A1* | 7/2021 | Ammerman | A61B 17/320016 |

* cited by examiner

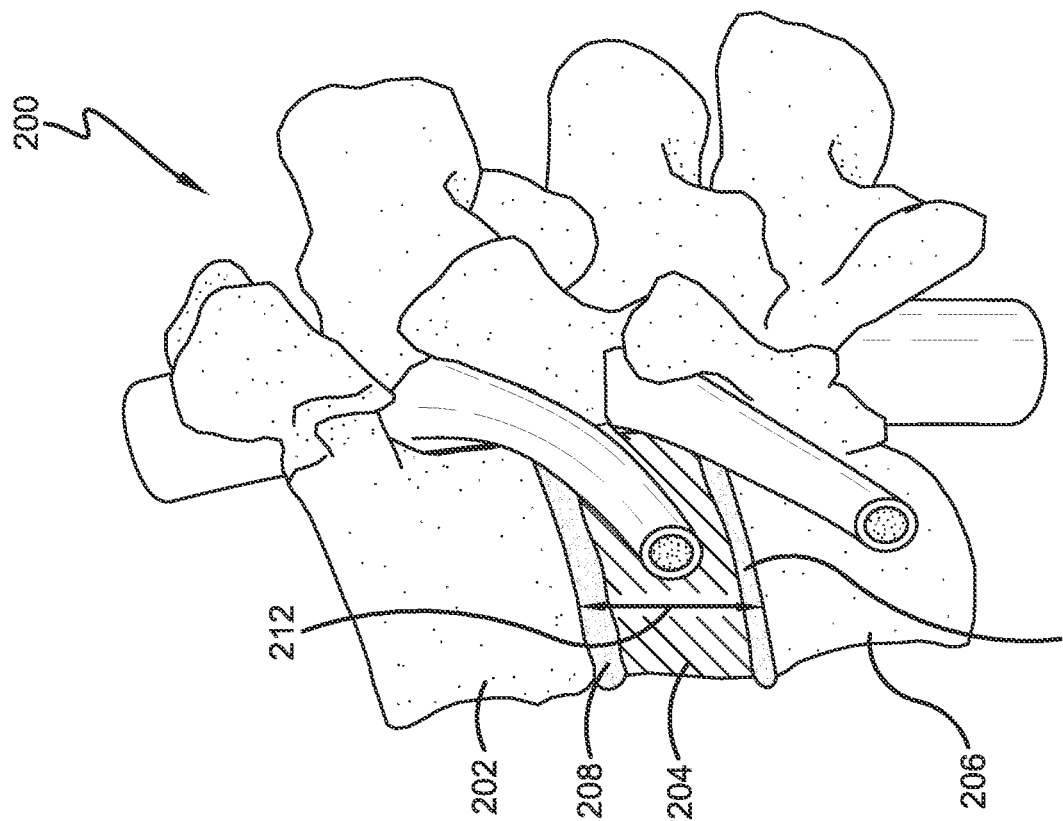
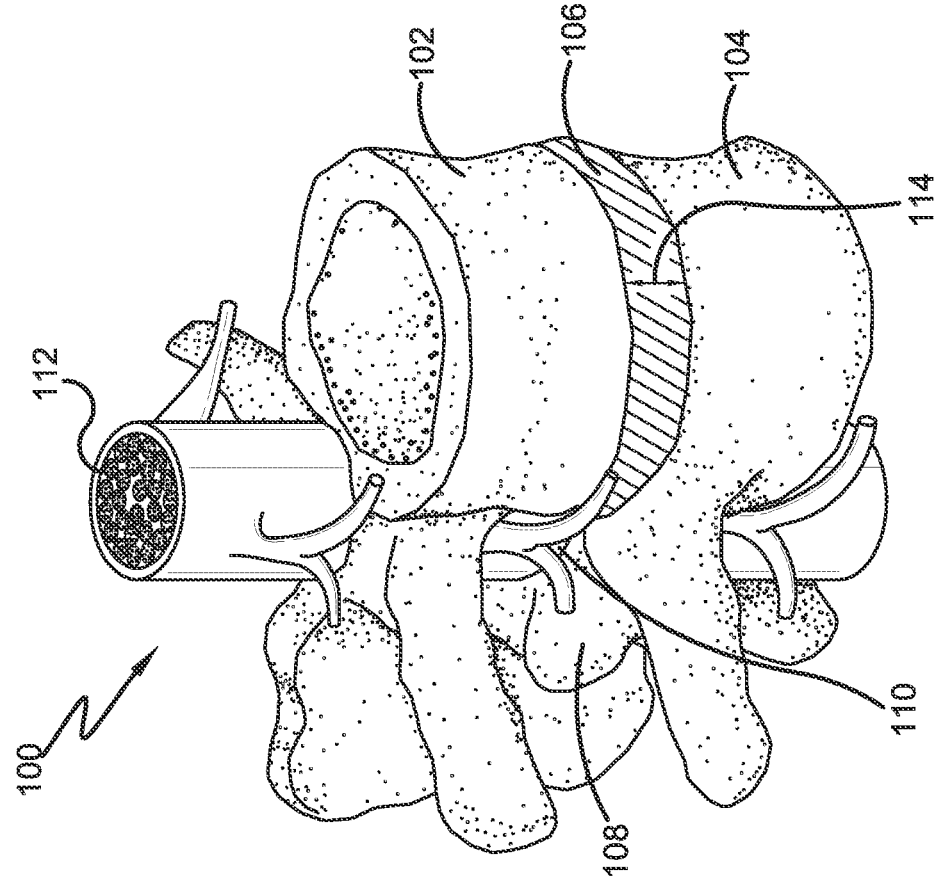

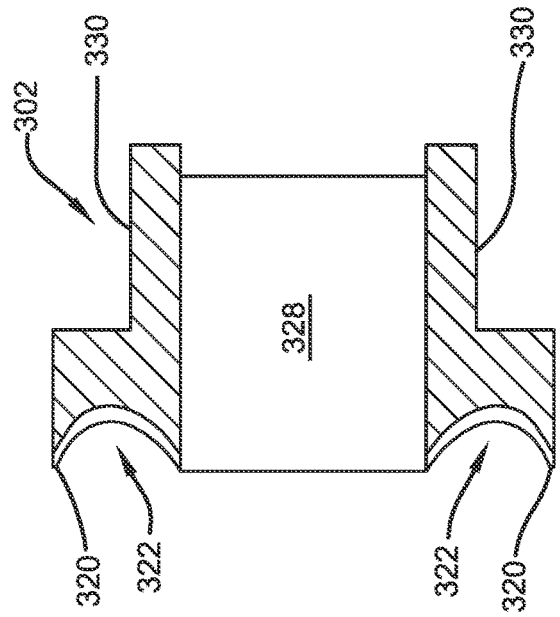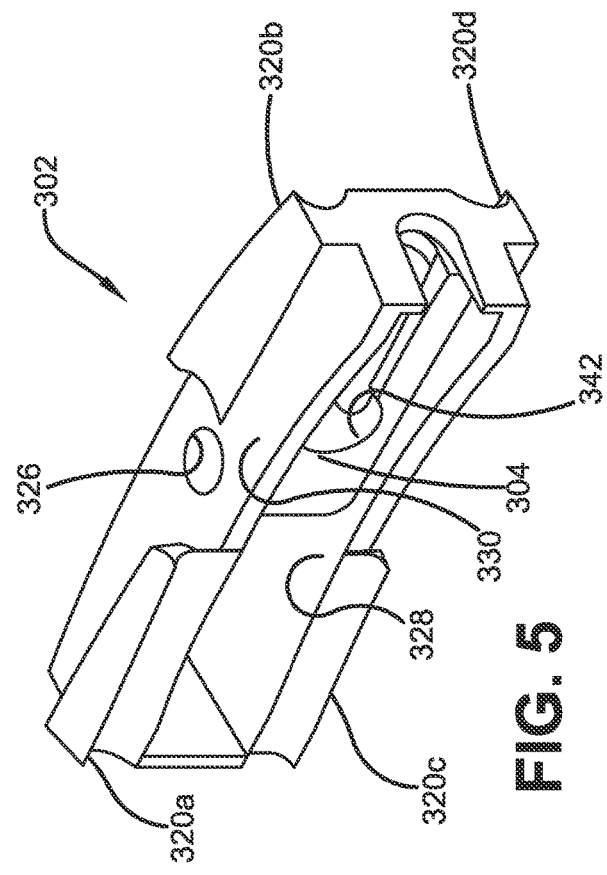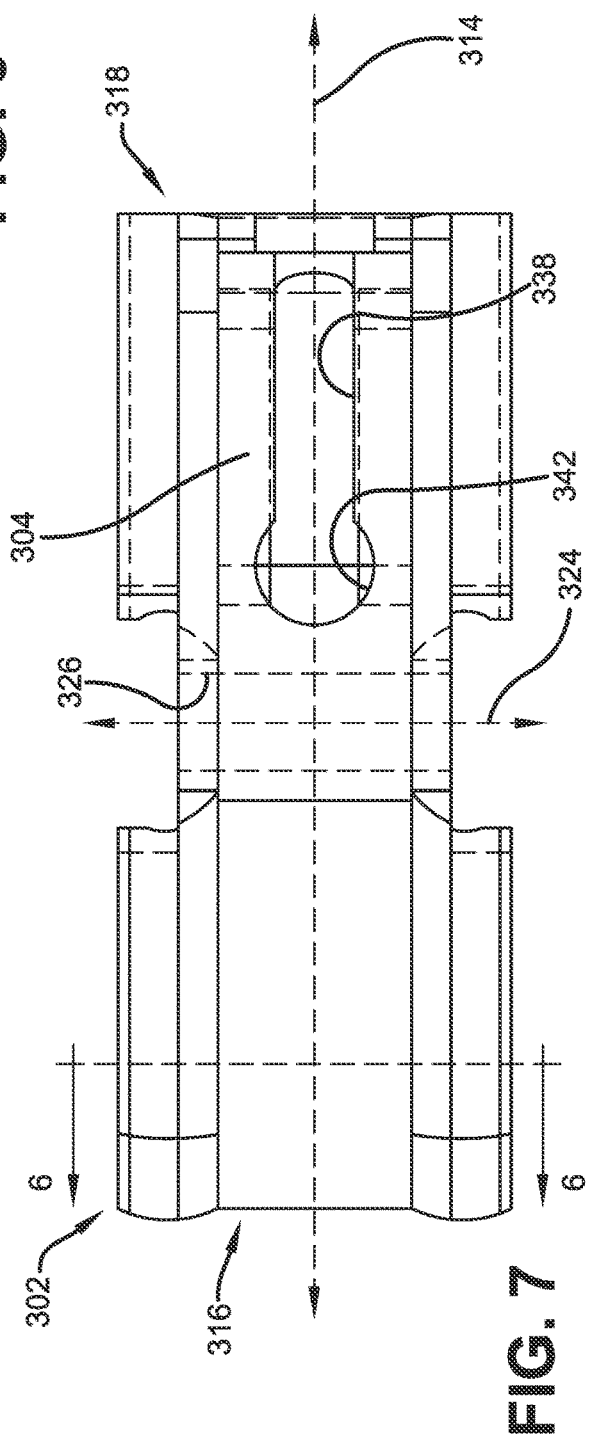

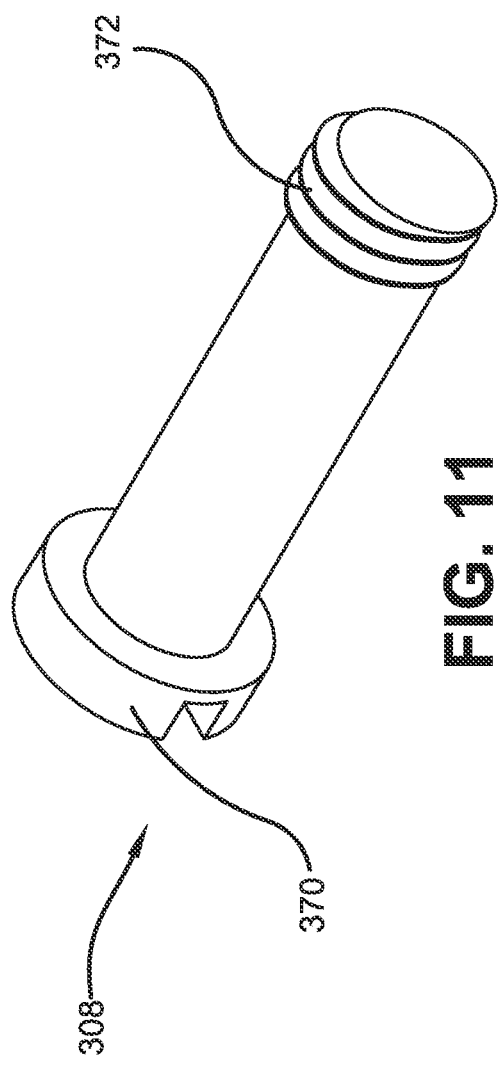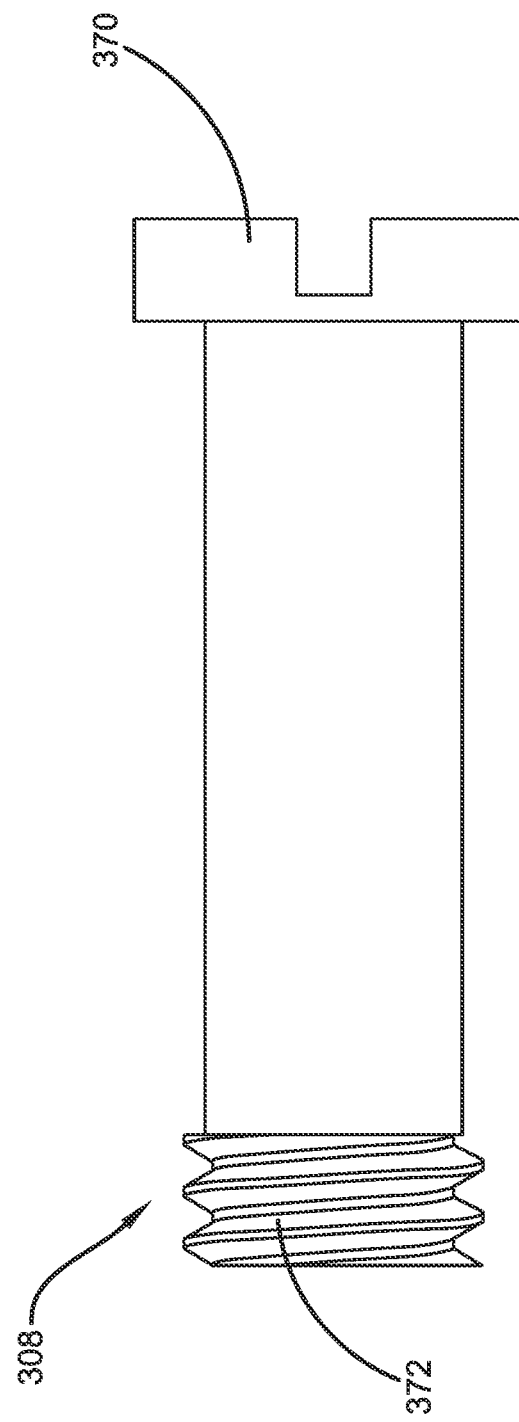

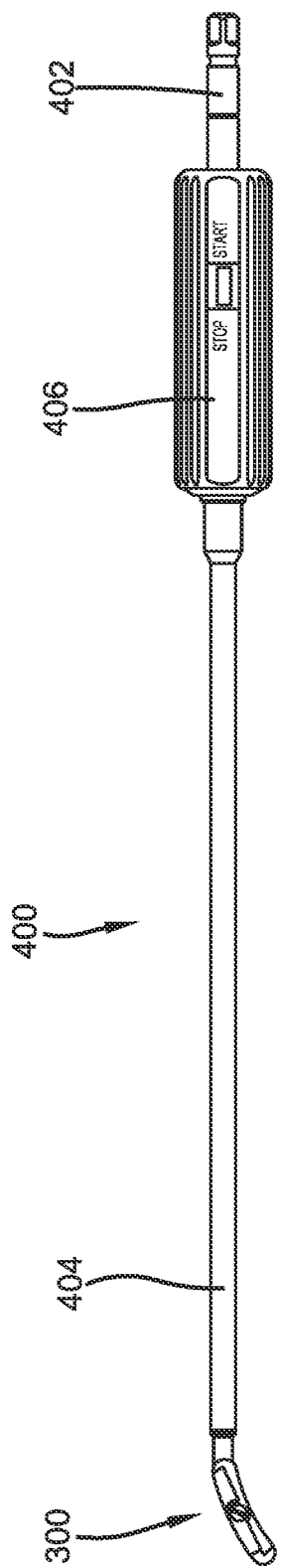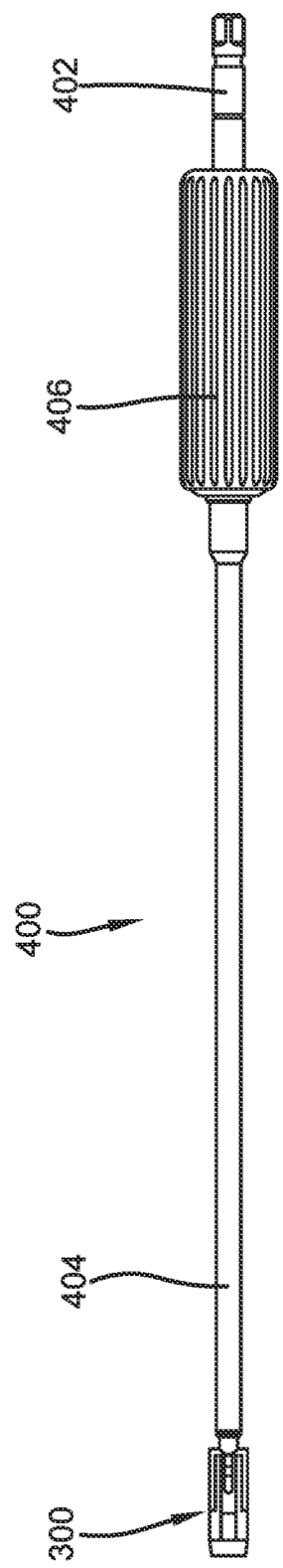
FIG. 13
FIG. 14

VERTEBRAL BODY SHAVER ASSEMBLY

This application claims the benefit of U.S. Provisional Application No. 62/954,141, titled VERTEBRAL BODY SHAVER INSTRUMENT, filed Dec. 27, 2019, the entirety of which is fully incorporated by reference herein.

BACKGROUND OF THE INVENTION

A. Field of Invention

This invention pertains to the art of methods and apparatuses regarding spine surgery and more specifically relates to surgical procedures and surgical instrumentation used during spine surgery.

B. Description of the Related Art

The volume of spinal surgeries to treat degenerative disc and facet disease has steadily increased over the past decades, fueled by population demographics and advancements in diagnostic and instrumentation adjuncts. Improvements in intraoperative radiological imaging and surgical technique have generated a great deal of interest in applying minimally invasive surgical (MIS) techniques to spinal applications. As in other surgical subspecialties, it is hoped such minimally invasive techniques applied to spinal surgery will result in less soft tissue trauma, less operative blood loss, reduced operative time, faster recovery periods and lower costs.

Known spinal surgical techniques, though generally working well for their intended purposes, have been adopted from traditional open surgical (non-MIS) techniques. As a result, known spinal surgical methods, instrumentation and interbody implants have limitations. One limitation is that the physical components are relatively large and bulky. This reduces surgeon visualization of the surgical site. Another limitation of known spinal surgical methods is that known surgical tools and implants are cumbersome and difficult to maneuver within the limited surgical space available. The limitations of current instrumentation in MIS spine surgery are noted particularly with regards to interbody fusion surgery.

Before any disc replacement device can be placed within the intradiscal space between two adjacent vertebral bodies, the vertebral body endplates need to be properly prepared. Specifically, the osteochondral material must be removed from the vertebral body endplates. While there are several known devices used for this purpose, there is a need for a vertebral body endplate shaver that can be inserted into the intradiscal space in a non-expanded condition, ideal for MIS application, and then adjusted into an expanded condition for purposes of shaving. In some embodiments, shaving can also occur when the shaver is adjusted from the expanded condition back to the non-expanded condition.

SUMMARY OF THE INVENTION

According to some embodiments of this invention, a vertebral body shaver assembly may comprise: a shaver inserter including: 1) an inserter housing having an opening; 2) a shaft: (a) received in the opening in the inserter housing; (b) having proximal and distal ends; and 3) a handle operatively engaged to the proximal end of the shaft; and a shaver instrument including: 1) a shaver housing; and 2) a blade support device: (a) that supports a first blade; (b) that is pivotal with respect to the shaver housing about a pivot axis; and (c) that is operatively engaged to the distal end of the shaft; wherein: 1) the shaver inserter is adapted to insert the shaver instrument into an intradiscal space between first and second vertebral body endplates in a non-expanded condition where a first endplate facing surface of the shaver housing and a first endplate facing surface of the blade support device together define a first effective footprint area A1 with respect to the vertebral body endplates; 2) after the shaver housing and the blade support device are properly positioned within the intradiscal space: (a) the handle is selectively operable to adjust the shaft to cause the blade support device to pivot about the pivot axis with respect to the shaver housing from the non-expanded condition to an expanded condition where the first endplate facing surface of the shaver housing and the first endplate facing surface of the blade support device together define a second effective footprint area A2 with respect to the vertebral body endplates; and (b) as the blade support device is selectively pivoted from the non-expanded condition to the expanded condition, the first blade is adapted to shave osteochondral material off the first vertebral body endplate; and (c) as the blade support device is selectively pivoted from the non-expanded condition to the expanded condition, the pivot axis remains perpendicular to the first and second vertebral body endplates; and 3) the ratio A2/A1 is at least 1.05.

According to some embodiments of this invention, a vertebral body instrument may comprise: a shaver housing; and a blade support device: 1) that supports a first blade; and 2) that is pivotal with respect to the shaver housing about a pivot axis; wherein: 1) the vertebral body shaver instrument is adapted to be inserted into an intradiscal space between first and second vertebral body endplates in a non-expanded condition where a first endplate facing surface of the shaver housing and a first endplate facing surface of the blade support device together define a first effective footprint area A1 with respect to the vertebral body endplates; 2) after the shaver housing and the blade support device are properly positioned within the intradiscal space: (a) the blade support device is selectively pivotal about the pivot axis with respect to the shaver housing from the non-expanded condition to an expanded condition where the first endplate facing surface of the shaver housing and the first endplate facing surface of the blade support device together define a second effective footprint area A2 with respect to the vertebral body endplates; and (b) as the blade support device is selectively pivoted from the non-expanded condition to the expanded condition, the first blade is adapted to shave osteochondral material off the first vertebral body endplate; and (c) as the blade support device is selectively pivoted from the non-expanded condition to the expanded condition, the pivot axis remains perpendicular to the first and second vertebral body endplates; and 3) the ratio A2/A1 is at least 1.05.

According to some embodiments of this invention, a vertebral body shaver method comprising the steps of: A) providing a shaver inserter including: 1) an inserter housing having an opening; 2) a shaft: (a) received in the opening in the inserter housing; (b) having proximal and distal ends; and 3) a handle operatively engaged to the proximal end of the shaft; B) providing a shaver instrument including: 1) a shaver housing; and 2) a blade support device: (a) that supports a first blade; (b) that is pivotal with respect to the shaver housing about a pivot axis; and (c) that is operatively engaged to the distal end of the shaft; C) providing the shaver inserter to be operable to insert the shaver instrument anterolaterally, posteriorly, or posterolaterally into an intradiscal space between first and second vertebral body endplates in a non-expanded condition where a first endplate facing surface of the shaver housing and a first endplate facing surface of the blade support device together define a first effective footprint area A1 with respect to the vertebral body endplates; D) providing the handle, after the shaver housing and the blade support device are properly positioned within the intradiscal space, to be operable to adjust the shaft to cause the blade support device to pivot about the pivot axis with respect to the shaver housing from the non-expanded condition to an expanded condition where the first endplate facing surface of the shaver housing and the first endplate facing surface of the blade support device together define a second effective footprint area A2 with respect to the vertebral body endplates; and wherein: 1) the ratio A2/A1 is at least 1.05; and 2) step D includes the steps of: (a) providing the first blade to be operable to shave osteochondral material off the first vertebral body endplate; and (b) maintaining the pivot axis in an orientation perpendicular to the first and second vertebral body endplates.

Benefits and advantages of the invention will become apparent to those skilled in the art to which it pertains upon a reading and understanding of the following detailed specification.

BRIEF DESCRIPTION OF THE DRAWINGS

The invention may take physical form in certain parts and arrangement of parts, embodiments of which will be described in detail in this specification and illustrated in the accompanying drawings which form a part hereof and wherein:

FIG. 1 is a side perspective view of a spinal segment showing a vertebral space defined by the intradiscal space usually occupied by a disc between two adjacent vertebral bodies.

FIG. 2 is a side perspective view of a spinal segment showing a vertebral space defined by the space usually occupied by a vertebral body and its two adjacent discs.

FIG. 5 is a perspective view of a blade support device.

FIG. 6 is a view taken along the line 6-6 of FIG. 7.

FIG. 7 is a side view of the blade support device shown in FIG. 5.

FIG. 11 is a perspective view of a pivot pin in the form of a fastener.

FIG. 12 is a side view of the pivot pin shown in FIG. 11.

FIG. 13 is a top view of a vertebral body shaver assembly.

FIG. 14 is a side view of the vertebral body shaver assembly shown in FIG. 13.

DETAILED DESCRIPTION

Figure 3:
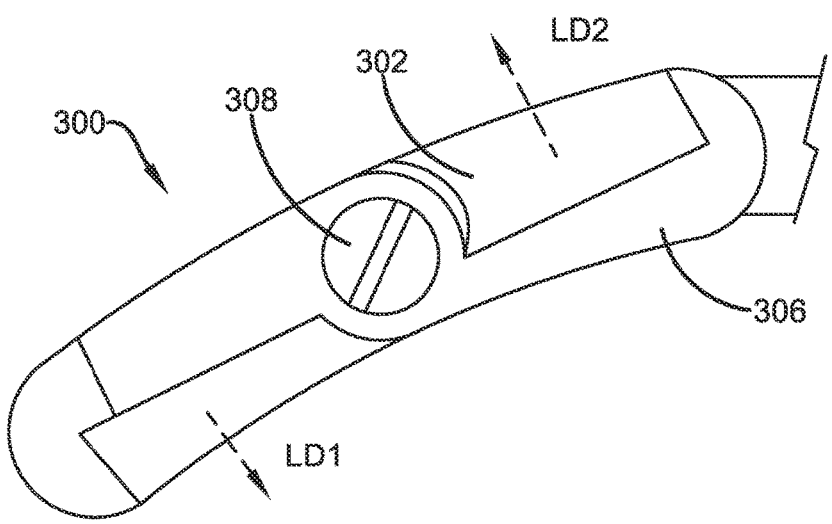
FIG. 3 is a top view of a shaver instrument in a contracted condition.

Referring now to the drawings wherein the showings are for purposes of illustrating embodiments of the invention only and not for purposes of limiting the same, FIG. 1 illustrates a spinal segment 100 made up of two vertebral bodies 102, 104 attached together by ligaments with a disc 106 separating them. Facet joints 108 fit between the two vertebral bodies 102, 104 and allow for movement. The neural foramen 110 between the vertebral bodies 102, 104 allow space for the nerve roots to travel freely from the spinal cord 112 to the body. If it is required to remove the disc 106 and replaced it with a disc replacement device, such as an implant, the space occupied by the disc, the intradiscal space between the two adjacent vertebral bodies 102, 104, defines the vertebral space 114. With reference now to FIG. 2, a spinal segment 200 may be made up of three vertebrae 202, 204, 206 attached together by ligaments. If it is required to remove the middle vertebra 204 (it is shown diseased) along with the adjacent discs 208, 210, such as may be required because of a corpectomy defect, and replaced them with a disc replacement device, the space between the two outer vertebral bodies 202, 206, defines the vertebral space 212. As the components and operation of a spinal column is well known to those of skill in the art, further detail will not be provided here.

With reference now to FIGS. 1-2, once the surgeon decides what type, style and size of disc replacement device is to be inserted, the vertebral space 114, 212 is prepared for insertion of the implant. This preparation may include discectomy using any steps and instruments chosen with the sound judgement of a person of skill in the art. Once the majority of intradiscal material is removed, a shaver instrument according to embodiments of this invention may be positioned within the vertebral space 114, 212 and used to make graduated cuts in the periphery of the endplates to remove the normal concave tapering of the bony endplate towards the periphery of the vertebrae—in other words, to remove the osteochondral material off the vertebral body endplates. This process insures true distraction of the vertebral space 114, 212 from the center.

Figure 4:
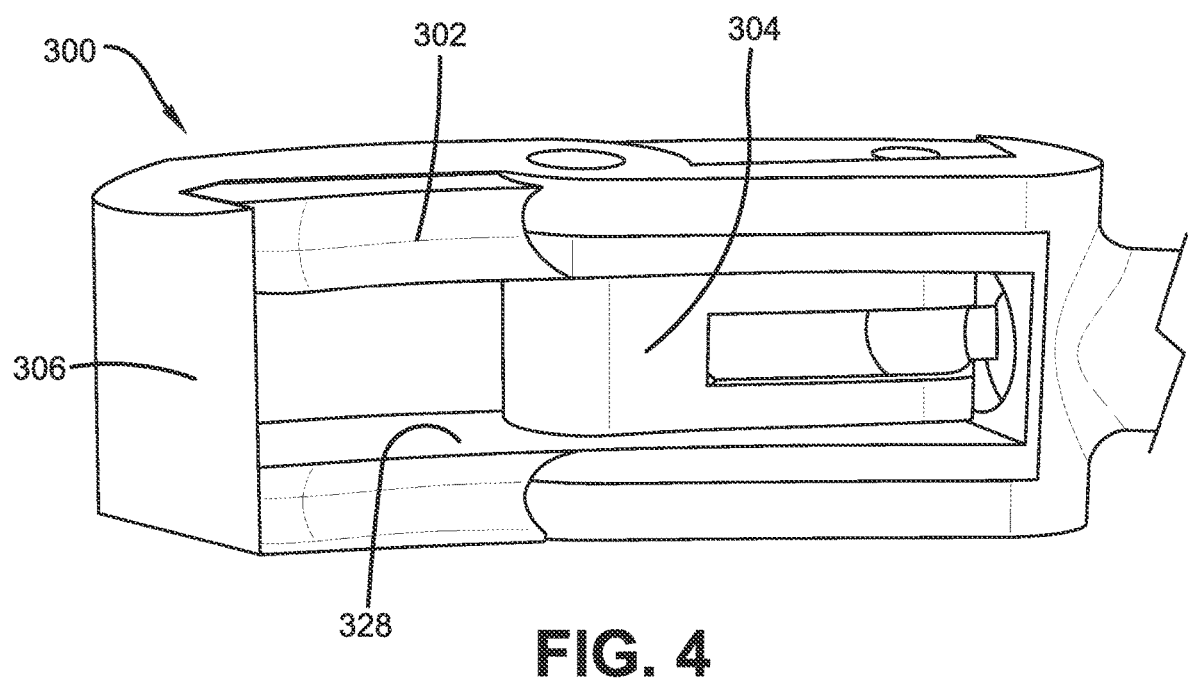
FIG. 4 is a side view of a shaver instrument in a contracted condition.
Figure 9:
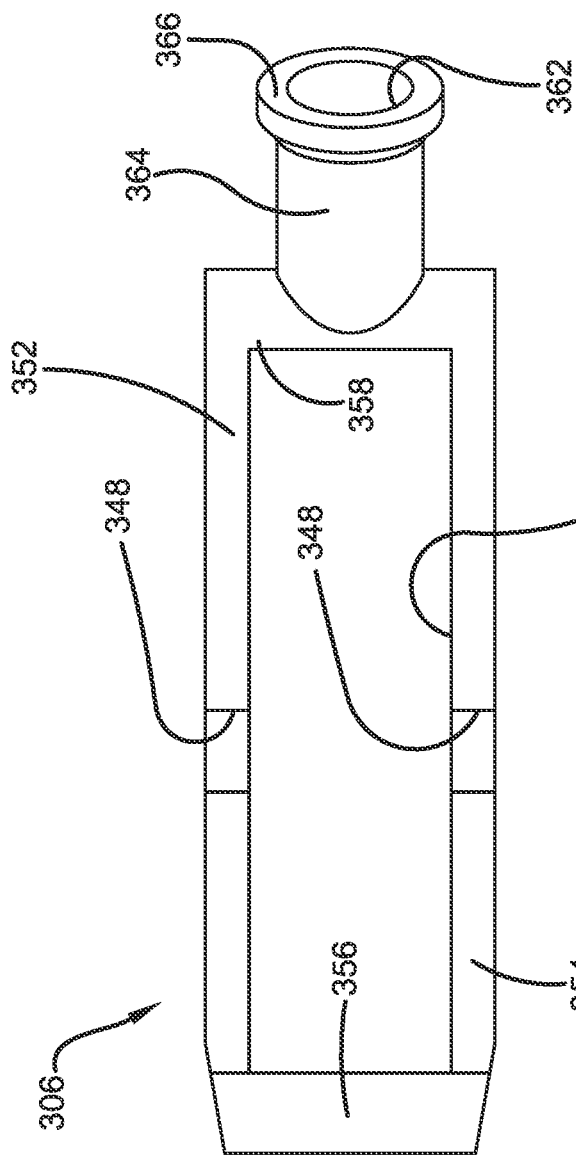
FIG. 9 is a side view of the shaver housing shown in FIG. 8.
Figure 10:
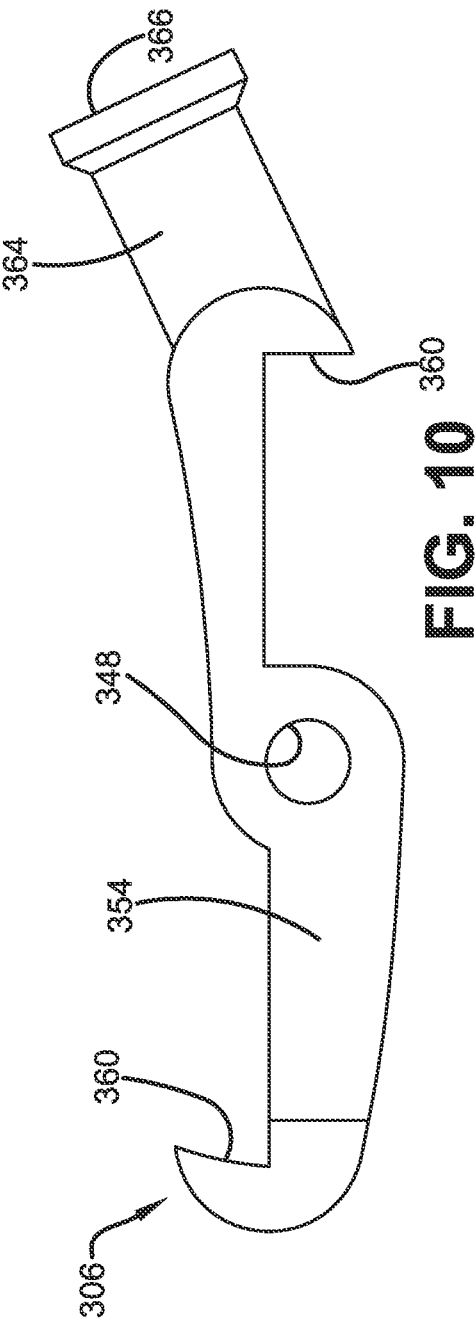
FIG. 10 is a bottom view of the shaver housing shown in FIG. 8.
Figure 8:
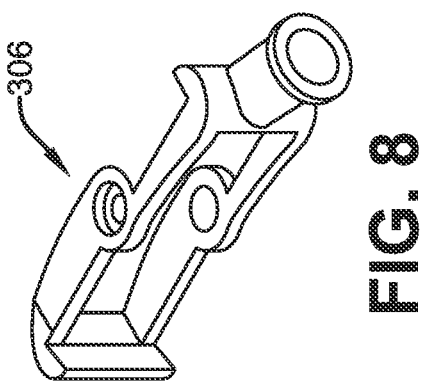
FIG. 8 is a perspective view of a shaver housing.
Figure 15:
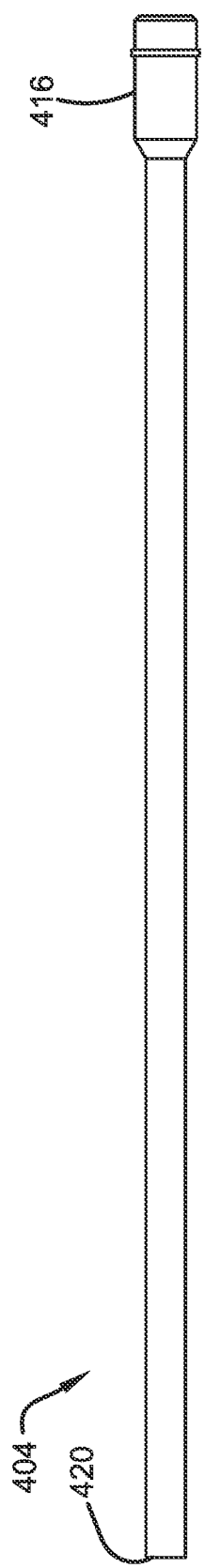
FIG. 15 is a side view of an inserter housing.
Figure 16:
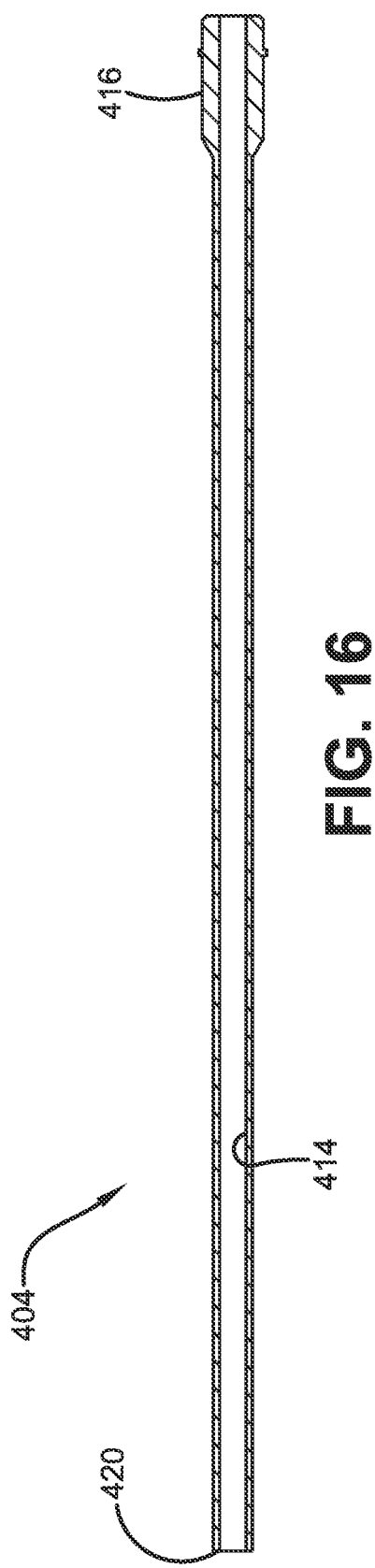
FIG. 16 is a sectional view of the inserter housing shown in FIG. 15.
Figure 18:
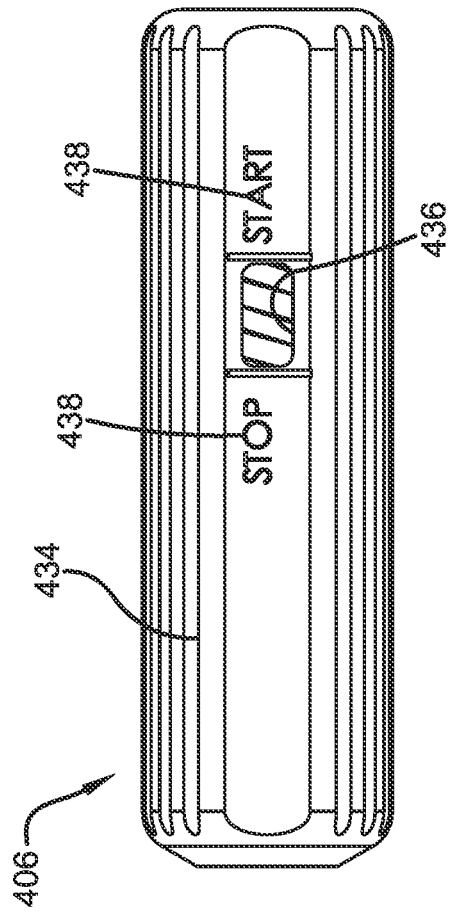
FIG. 18 is a side view of the handle shown in FIG. 17.
Figure 19:
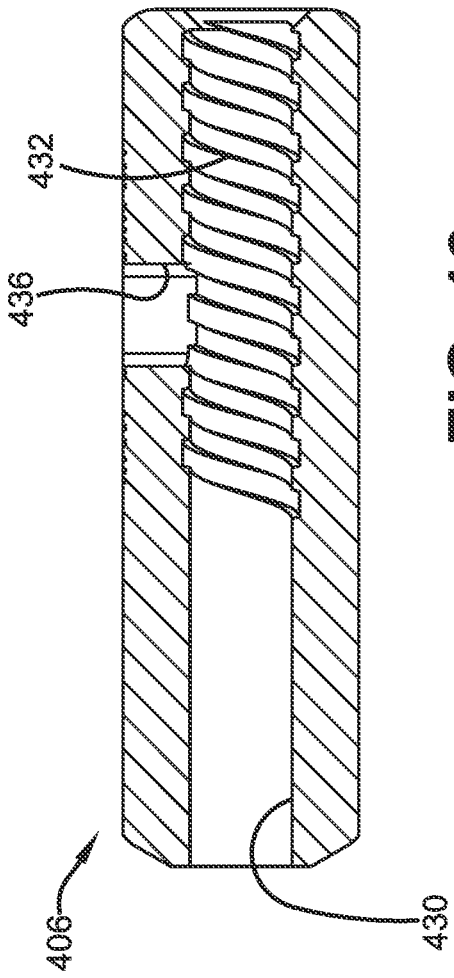
FIG. 19 is a sectional view of the handle shown in FIG. 18.
Figure 17:
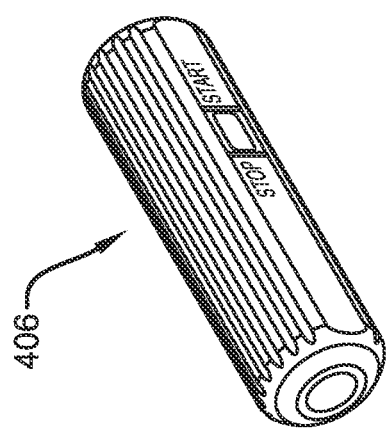
FIG. 17 is a perspective view of a handle.

A vertebral body shaver assembly may include a shaver inserter and a shaver instrument. With reference now to FIGS. 3-4, shaver instrument 300 may include a blade support device 302 and a shaver housing 306. The shaver instrument 300 may be used to shave/cut at least one of the spinal endplates. It should be noted, however, that in some embodiments the shaver instrument 300 may be used to shave/cut both spinal endplates independently and in yet other embodiments the shaver instrument 300 may be used to shave/cut both spinal endplates simultaneously. In some embodiments, the shaver instrument 300 may have an outside shape and size similar to a spinal implant. Non-limiting examples of such implants are shown in U.S. Pat. No. 8,236,058 titled SPINE SURGERY METHOD AND IMPLANT which is incorporated herein by reference in its entirety.

Figure 30:
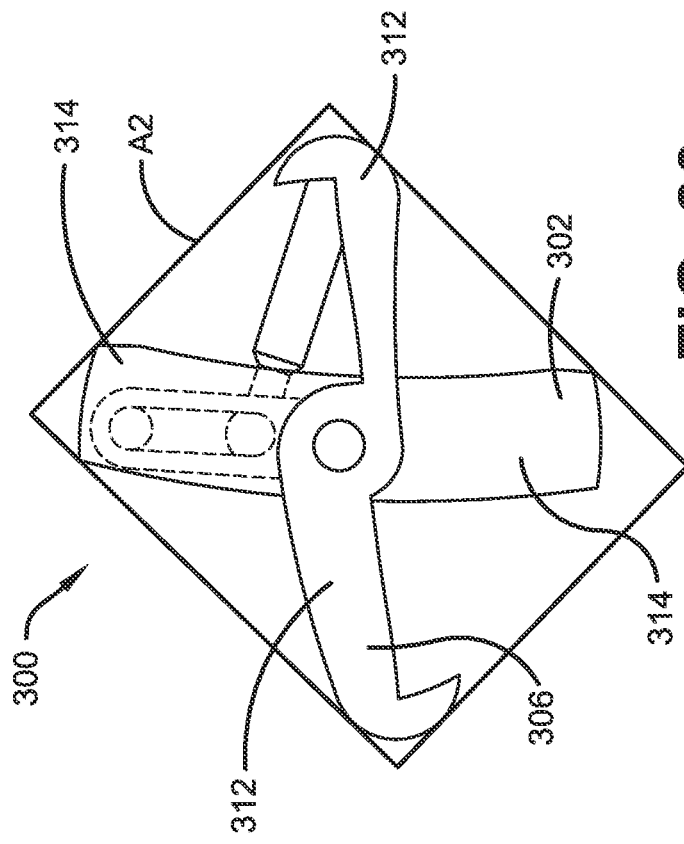
FIG. 30 is view similar to what is shown in FIG. 28 but illustrating effective footprint area A2.
Figure 29:
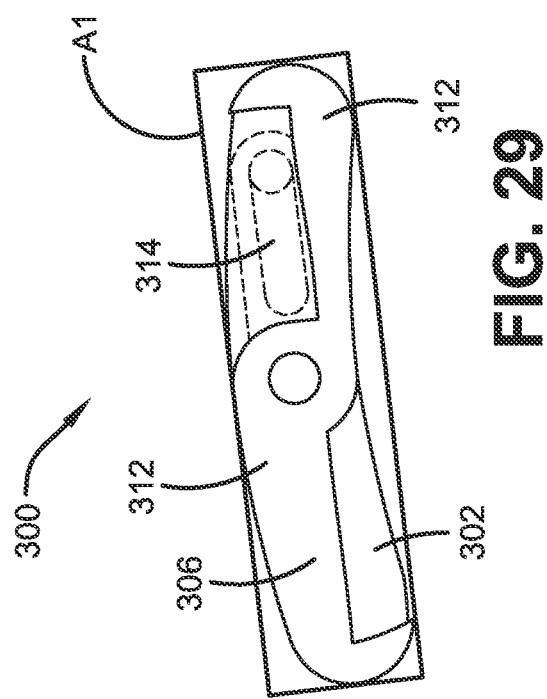
FIG. 29 is view similar to what is shown in FIG. 27 but illustrating effective footprint area A1.

The shaver instrument 300 may be adapted to be inserted into the intradiscal space 114, 212 (FIGS. 1-2) in a non-expanded condition (ideal for MIS application), as shown in FIG. 29, and then adjusted into an expanded condition while within the intradiscal space 114, 212, as shown in FIG. 30. In some embodiments, shown, this adjustment between the non-expanded condition and the expanded condition may be accomplished by pivoting the blade support device 302 with respect to the shaver housing 306 about pivot axis 324, shown in FIG. 7. When in the non-expanded condition, the endplate facing surface 312 of the shaver housing 306 and the endplate facing surface 314 of the blade support device 302 may together define a first effective footprint area A1 with respect to the vertebral body endplates. When in the expanded condition, the endplate facing surface 312 of the shaver housing 306 and the endplate facing surface 314 of the blade support device 302 may together define a second effective footprint area A2 with respect to the vertebral body endplates. For purposes of this patent, "effective footprint area" is defined as the area of the smallest rectangle that would encompass or surround the endplate facing surfaces 312 and 314, as shown, where the rectangle perimeter contacts the shaver instrument 300 perimeter at a minimum of two points. By "smallest rectangle" it is meant the rectangle having the smallest possible area. Thus, for example, if the endplate facing surfaces 312 and 314 together are rectangular in shape with a width W and a length L, the effective footprint area would be the area of rectangle with width W and length L (the effective footprint area would be W times L). If, as another example, the endplate facing surfaces 312 and 314 together are circular in shape with a diameter D, the effective footprint area would be the area of a square with sides having a length D (the effective footprint area would be D times D). As a general rule, the larger this ratio the easier for the surgeon to place the shaver instrument 300 into position within the intradiscal space 114, 212. In some embodiments, the ratio A2/A1 is at least 1.05. In other embodiments, the ratio A2/A1 is at least 1.3. In yet other embodiments, the ratio A2/A1 is at least 1.5. In still other embodiments, the ratio A2/A1 is at least 1.8. In some embodiments, the endplate facing surfaces are the same—or nearly so—facing the upper endplate as facing the lower endplate.

With reference now to FIGS. 1-7 and 27-28, blade support device 302 may support one or more blades 320 that are sharp enough and strong enough to shave or cut the osteochondral material off the corresponding vertebral body endplate. With reference to FIG. 7, the blade support device 302 may have a longitudinal axis 314 that is perpendicular to the pivot axis 324. The blade support device 302 may have a first longitudinal end 316 and a second longitudinal end 318 opposite the first longitudinal end 316. The pivot axis 324 may be positioned longitudinally between the first and second longitudinal ends 316, 318, as shown. In one embodiment, the pivot axis 324 may be positioned at or very near the longitudinal center of the support device 302. In some embodiments, one or more blades 320 may be positioned on the first longitudinal end 316 and/or one or more blades 320 may be positioned on the second longitudinal end 318. With reference to FIGS. 5 and 7, for example, blades 320a and 320c are positioned on the first longitudinal end 316 and blades 320b and 320d are positioned on the second longitudinal end 318. In some embodiments, one or more blades 320 may generally extend in one or more linear direction(s). With reference to FIGS. 3 and 5, for example, blades 320a and 320c extend in linear direction LD1 and blades 320b and 320d extend in linear direction LD2. In some embodiments, one or more blades 320 may be positioned to shave osteochondral material off one vertebral body endplate (with reference to FIGS. 1-2, the upper or lower endplate) and/or one or more blades 320 may be positioned to shave osteochondral material off the other vertebral body endplate (with reference to FIGS. 1-2, the lower or upper endplate). With reference to FIG. 5, for example, blades 320a and 320b are positioned to shave osteochondral material off one vertebral body endplate (upper endplate as shown) and blades 320c and 320d are positioned to shave osteochondral material off the other vertebral body endplate (lower endplate as shown).

Figure 28:
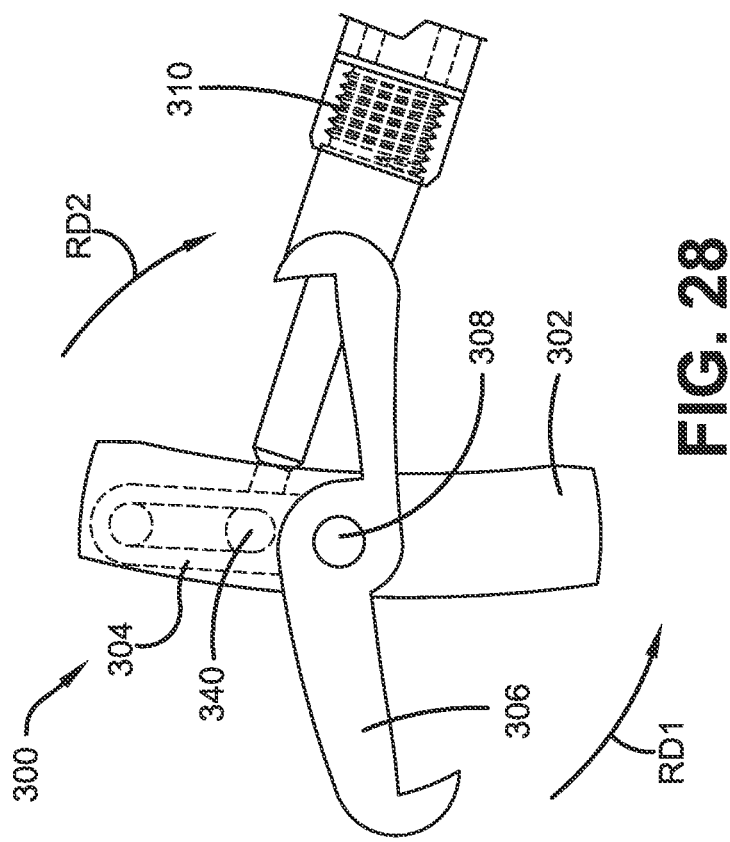
FIG. 28 is a top view of the shaver instrument shown in FIG. 27 but in an expanded condition.
Figure 27:
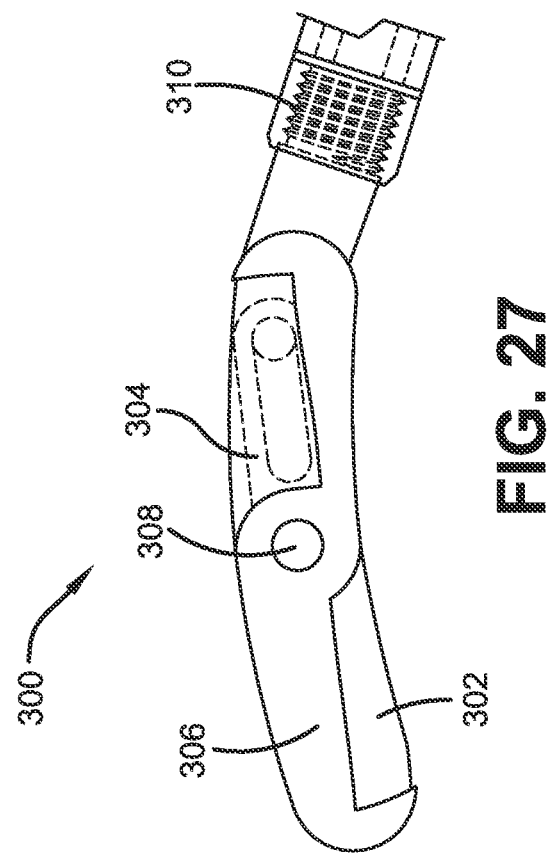
FIG. 27 is a top view of a shaver instrument in a contracted condition.

With reference now to FIGS. 3, 5-7 and 27-28, in some embodiments one or more blades 320 may shave one or more vertebral body endplates when the blade support device 302 is pivoted with respect to the shaver housing 306 about pivot axis 324 in one rotational direction while in other embodiments one or more blades 320 may shave one or more vertebral body endplates when the blade support device 302 is pivoted with respect to the shaver housing 306 about pivot axis 324 in both rotational directions. With reference to FIGS. 5 and 27-28, for example, blades 320a, 320b, 320c and 320d are all positioned to shave osteochondral material off one of the vertebral body endplates only when the blade support device 302 is pivoted with respect to the shaver housing 306 about pivot axis 324 in first rotational direction RD1. The first rotational direction RD1 is the direction that enables the blade support device 302 to pivot about the pivot axis 324 with respect to the shaver housing 306 from the non-expanded condition (FIG. 27) to the expanded condition (FIG. 28). With this arrangement, when the blade support device 302 is pivoted about the pivot axis 324 with respect to the shaver housing 306 in the second rotation direction RD2 from the expanded condition (FIG. 28) to the non-expanded condition (FIG. 27), no shaving occurs. This enables the surgeon to re-position the shaver instrument 300 as required. This arrangement also permits the surgeon to shave different portions of one and/or the other vertebral body endplates. With reference to FIGS. 3, 5 and 27-28, for example, blade 320a shaves a first portion of a first vertebral body endplate while blade 320b simultaneously shaves a second distinct portion of the same first vertebral body endplate. Similarly, blade 320c shaves a first portion of a second vertebral body endplate while blade 320d simultaneously shaves a second distinct portion of the same second vertebral body endplate. In some embodiments, see FIG. 6, juxtaposed to one or more blades 320 is a curved concave surface 322 that provides a surface for the shaved vertebral material to slide on as it is removed from the vertebral endplate.

With reference now to FIGS. 7 and 27-28, the amount of pivoting required to move the blade support device 302 with respect to the shaver housing 306 about pivot axis 324 in rotational direction RD1 from the non-expanded condition (FIG. 27) to the expanded condition (FIG. 28) and in rotational direction RD2 from the expanded condition (FIG. 28) to the non-expanded condition (FIG. 27) can be any amount chosen with the sound judgement of a person of skill in the art. In some embodiments, the blade support device 302 pivots about the pivot axis 324 with respect to the shaver housing 306 at least 25 degrees. In some embodiments, the blade support device 302 pivots about the pivot axis 324 with respect to the shaver housing 306 at least 35 degrees. In some embodiments, the blade support device 302 pivots about the pivot axis 324 with respect to the shaver housing 306 at least 45 degrees. In some embodiments, the blade support device 302 pivots about the pivot axis 324 with respect to the shaver housing 306 at least 55 degrees. In some embodiments, the blade support device 302 pivots about the pivot axis 324 with respect to the shaver housing 306 at least 65 degrees. In some embodiments, the blade support device 302 pivots about the pivot axis 324 with respect to the shaver housing 306 at least 75 degrees. In some embodiments, the blade support device 302 pivots about the pivot axis 324 with respect to the shaver housing 306 at least 85 degrees. In some embodiments, the blade support device 302 pivots about the pivot axis 324 with respect to the shaver housing 306 at least 95 degrees. In some embodiments, the blade support device 302 pivots about the pivot axis 324 with respect to the shaver housing 306 at least 105 degrees. In some embodiments, the blade support device 302 pivots about the pivot axis 324 with respect to the shaver housing 306 at least 115 degrees. In some embodiments, the blade support device 302 pivots about the pivot axis 324 with respect to the shaver housing 306 at least 125 degrees. In some embodiments, the blade support device 302 pivots about the pivot axis 324 with respect to the shaver housing 306 at least 135 degrees. In some embodiments, the blade support device 302 pivots about the pivot axis 324 with respect to the shaver housing 306 at least 145 degrees. In some embodiments, the blade support device 302 pivots about the pivot axis 324 with respect to the shaver housing 306 at least 155 degrees. In some embodiments, the blade support device 302 pivots about the pivot axis 324 with respect to the shaver housing 306 at least 165 degrees. In some embodiments, the blade support device 302 pivots about the pivot axis 324 with respect to the shaver housing 306 at least 175 degrees. In the embodiment shown, the blade support device 302 pivots about the pivot axis 324 with respect to the shaver housing 306 about 90 degrees.

With reference now to FIGS. 3-7 and 26-28, as noted above, the adjustment between the non-expanded condition and the expanded condition may be accomplished by pivoting the blade support device 302 with respect to the shaver housing 306 about pivot axis 324. This pivoting action may be accomplished in any manner chosen with the sound judgement of a person of skill in the art. In some embodiments, the blade support device 302 may have an opening 326 that receives a pivot pin 308, discussed further below, that defines the pivot axis 234. In some embodiments, the blade support device 302 may have a groove 338 to receive an insert member 340, discussed further below. The groove 338 may have a length along which the insert member 340 travels to cause the rotational movement. In some embodiments, the insert member 340 may be substantially spherical in shape, as shown. The groove 338 may have a pivot location 342 that permits the insert member 340 to pivot within the pivot location 342 when the insert member 340 is in the pivot location 342. The pivot location 342, in some embodiments, may be on a longitudinally inward end of the groove 338, as shown. In some embodiments, the groove's length may extend along the longitudinal axis 314, as shown. In some embodiments, the groove 338 may be formed in a portion of the blade support device 302 considered a hinge swivel 304. The blade support device 302 may have a reception zone 328 that receives the hinge swivel 304, as shown. The reception zone 328 may be larger than the hinge swivel 304, as shown, reducing the weight of the blade support device 302. In some embodiments, the hinge swivel 304 is made independent to the rest of the blade support device 302 and may be attached via a press-fit. In other embodiments, the hinge swivel 304 is made along with the rest of the blade support device 302 as a single component. The hinge swivel 304 may have, with reference to FIG. 26, an opening 336 that defines part of previously noted opening 326. The upper and lower surfaces of the blade support device 302 may have cutout sections 330 to receive portions of the shaver housing 306, discussed further below.

With reference now to FIGS. 4 and 8-12, shaver housing 306 may be designed to support the blade support device 302 to the shaver inserter, which will be discussed further below. The shaver housing 306 may have a reception zone 350 designed to receive the blade support device 302. In one embodiment, shown, the reception zone 350 is defined by upper wall 352, lower wall 354, and two opposing side walls 356, 358. The upper and lower walls 356, 358 may have cutouts 360, as shown, that receive the upper and lower surfaces of the blade support device 302. In this way, the most upper and most lower surfaces of both the shaver housing 306 and the blade support device 302 may be substantially coplanar, as shown in FIG. 4. The shaver housing 306 may have an opening 348 that receives the pivot pin 308. For the embodiment shown, opening 348 extends through the upper and lower walls 356, 358. The shaver housing 306 may have an opening 362 that enables the shaver inserter to connect to the rotatory blade 302. In some embodiments, shown, opening 362 is within a tube section 364 that extends proximally from side wall 358. The distal end of the tube section 364 may have a distally facing surface 366. In some embodiments, the pivot pin 308 may be a fastener. In some embodiments, shown in FIGS. 11-12, fastener 308 may have a head 370 that receives a tool at one end and threads 372 at the opposite end. Fastener 308 may be received in opening 348 of the shaver housing 306 and opening 326 of the blade support device 302 in order to attach the blade support device 302 to the shaver housing 306. In some embodiments, the threads 372 engage matching threads that define opening 348 within lower wall 354 of the shaver housing 306 in a known manner.

Figure 22:
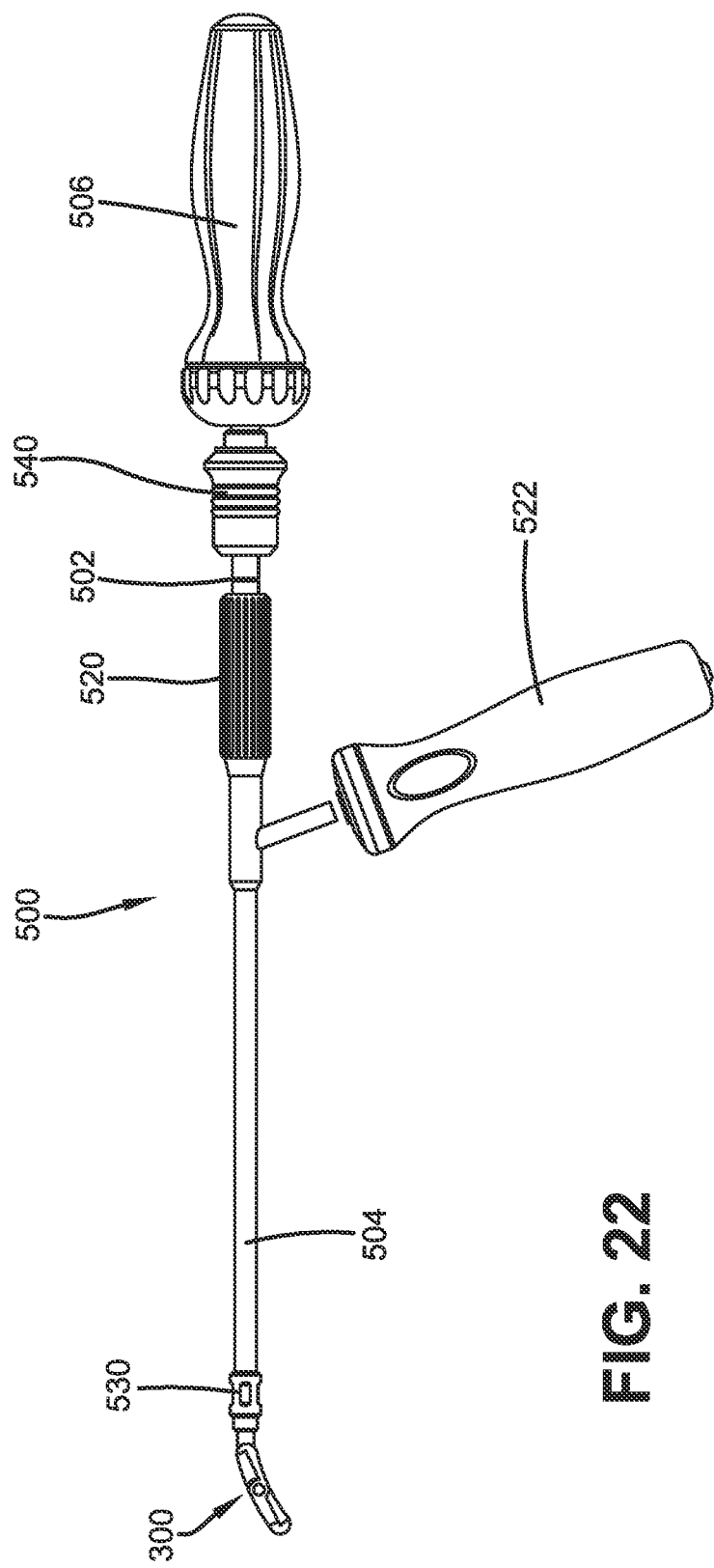
FIG. 22 is a top view of a vertebral body shaver assembly.
Figure 23:
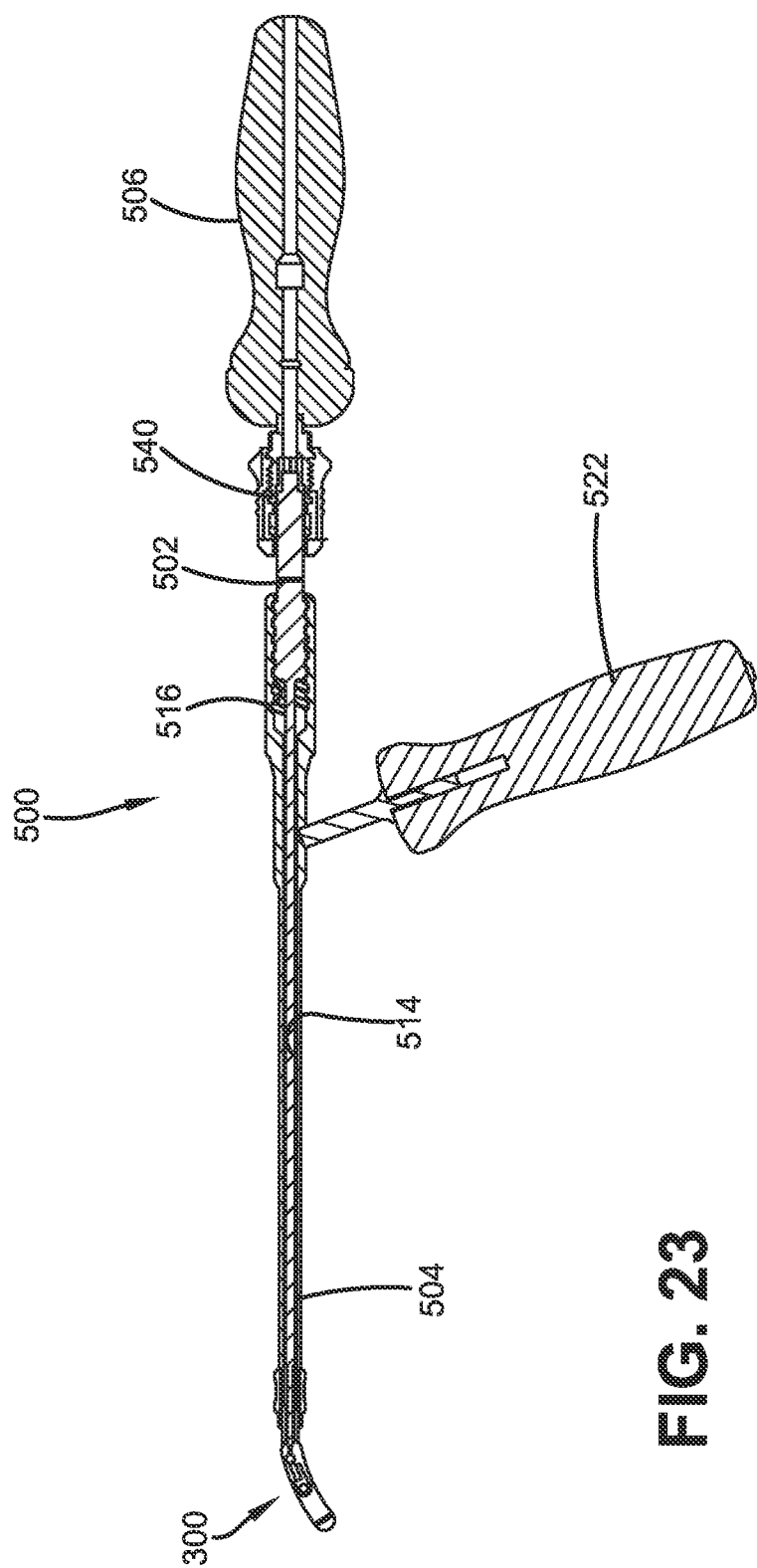
FIG. 23 is a section view of the of the vertebral body shaver assembly of FIG. 22.
Figure 24:
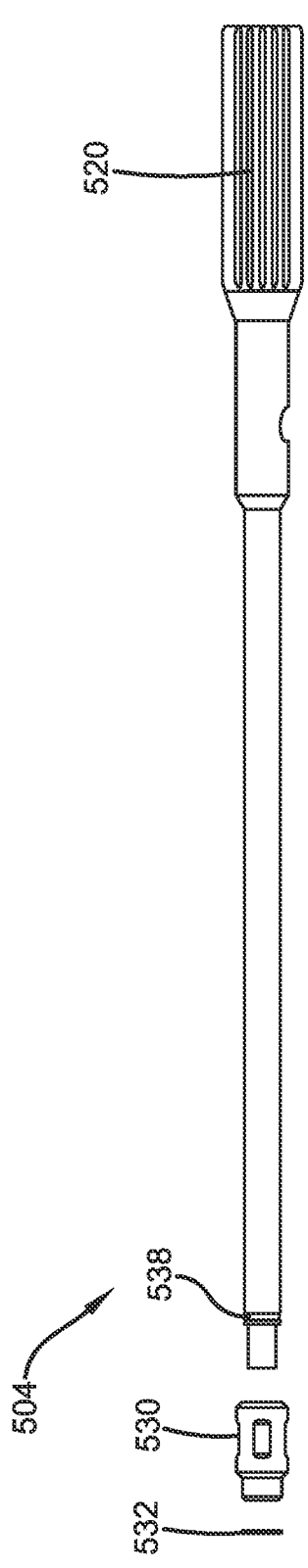
FIG. 24 is a side view of an inserter housing.

With reference now to FIGS. 1-2, 13-14 and 27-28, a shaver inserter may be used to insert the shaver instrument 300 into the vertebral space 114, 212. In some embodiments, the shaver inserter may be used to positioned the shaver instrument 300 within the vertebral space in a non-deployed or contracted condition, as shown in FIG. 27, and then may be used to adjust the shaver instrument 300 within the vertebral space into a deployed or expanded condition, as shown in FIG. 28. Once inserted, the shaver instrument 300 may be adjusted between the contracted condition and the expanded condition to achieve shaving/cutting of the desired vertebral material. FIGS. 13-14 show embodiments of shaver inserter 400 and FIGS. 22-23 shows embodiments of shaver inserter 500.

With reference now to FIGS. 13-21, shaver inserter 400 may include a shaft 402, an inserter housing 404 and a handle 406. The distal end of shaft 402 may have previously described insert member 340 that may be substantially spherical in shape, as shown, and may be received in the groove 338 of the hinge swivel 304 (see FIGS. 4-5 and 7). By moving the shaft 402 along its longitudinal axis (distally and proximally), the insert member 340 moves within the groove 338. Once the insert member 340 is received within the pivot location 342, continued motion of the shaft 402 along its longitudinal axis causes the hinge swivel 304, and thus the blade support device 302, to pivot about pivot axis 324, enabling the blades 320 to shave/cut vertebral material from the spinal endplates.

Figure 20:
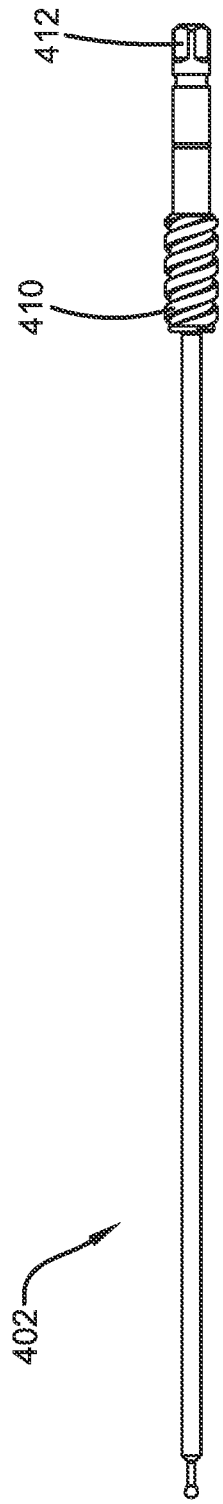
FIG. 20 is a side view of a shaft.
Figure 21:
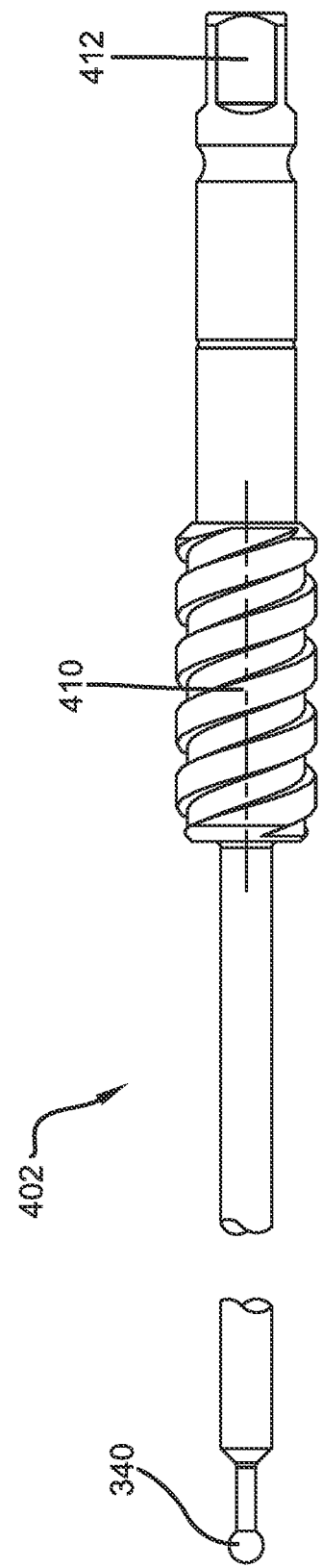
FIG. 21 is a side view of the shaft of FIG. 20 but shown partially discontinuous.

With reference now to FIGS. 20-21, the shaft 402 may have threads 410 on an outer surface of the shaft 402, as shown. The threads 410 may be used to engage later to be described threads in order to move the shaft 402 longitudinally. Threads 410 may be positioned anywhere on the shaft 402 chosen with the sound judgment of a person of skill in the art. In one embodiment, shown, they are positioned between the proximal and distal ends of the shaft 402. The shaft 402, in some embodiments, may have a tool reception surface 412 designed to receive a tool (not shown) having a matching surface that engages tool reception surface 412. The tool may be used, for example, to move the shaft 402 longitudinally and/or rotationally. In one embodiment, shown, the tool reception surface 412 is positioned on the proximal end of the shaft 402.

With reference now to FIGS. 13-16 and 20, inserter housing 404 may have an opening 414 that receives the shaft 402 and permits the shaft 402 to move within the opening 414 with respect to the housing 404. In one embodiment, shown, opening 414 extends the full length of the housing 404. This enables the distal end of the shaft 402 to extend distally beyond the distal end of the housing 404 and the proximal end of the shaft 402 to extend proximally beyond the proximal end of the housing 404. The housing 404 may have a handle attachment surface 416 that receives the handle 406 to attach the handle to the housing 404. In some embodiments, shown, the handle attachment surface 416 is positioned at the proximal end of the housing 404. The distal end of the housing 404 may have a contact surface 420. Contact surface 420 may be designed to contact surface 366 of the shaver housing 306, shown in FIGS. 9-10. In some embodiments, surfaces 420 and 366 may be coplanar and may be of the same, or similar, size and shape.

With reference now to FIGS. 13-14 and 17-21, handle 406 may have an opening 430 that receives the proximal ends of the housing 404 and the shaft 402 and permits the shaft 402 to move within the opening 430 with respect to the handle 406. In one embodiment, shown, opening 430 extends the full length of the handle 406. This enables the distal end of the shaft 402 to extend distally beyond the distal end of the handle 406 and the proximal end of the shaft 402 to extend proximally beyond the proximal end of the handle 406. A portion of the circumference of the opening 430 may include threads 432 designed to engage the threads 410 of the shaft 402. When thus engaged, rotation of the handle 406 about its longitudinal axis causes the shaft 402 to move along its longitudinal axis. Rotation of the handle 406 in one direction may cause the shaft 402 to move distally and rotation of the handle 406 in the opposite direction may cause the shaft 402 to move proximally. The outer surface of the handle 406 may have a grip surface 434 that makes it easier for the surgeon to grip the handle 406 when rotating the handle 406. In some embodiments, the handle 406 may have an opening 436 that extends from the opening 430 to the outer surface of the handle 406. This enables the surgeon to see the position of the shaft 402 at all times. The handle 406 may have one or more identification surfaces 438, two shown, that can be used to communicate to the surgeon the limits of the position of the handle 406.

With reference now to FIGS. 22-26, shaver inserter 500 may include a shaft 502, an inserter housing 504 and a handle 506. Shaft 502 may be similar to previously described shaft 402 with an insert member 340, threads 510 (similar to threads 410) and tool reception surface 512 (similar to tool reception surface 412). The use and operation of shaft 502 is similar to the use and operation of shaft 402 explained above, though differences will be described below.

With continuing reference to FIGS. 22-26, housing 504 may have an opening 514 that receives the shaft 502 and permits the shaft 502 to move within the opening 514 with respect to the housing 504. In one embodiment, shown, opening 514 extends the full length of the housing 504. This enables the distal end of the shaft 502 to extend distally beyond the distal end of the housing 504 and the proximal end of the shaft 502 to extend proximally beyond the proximal end of the housing 504. A portion of the circumference of the opening 514 may include threads 516 designed to engage the threads 510 of the shaft 502. The outer surface of the housing 504 may have a grip surface 520 that makes it easier for the surgeon to grip/hold the housing 504. In some embodiments, a second handle 522 may be attached to the housing 504 and used by the surgeon to grip/hold the inserter housing 504.

Figure 26:
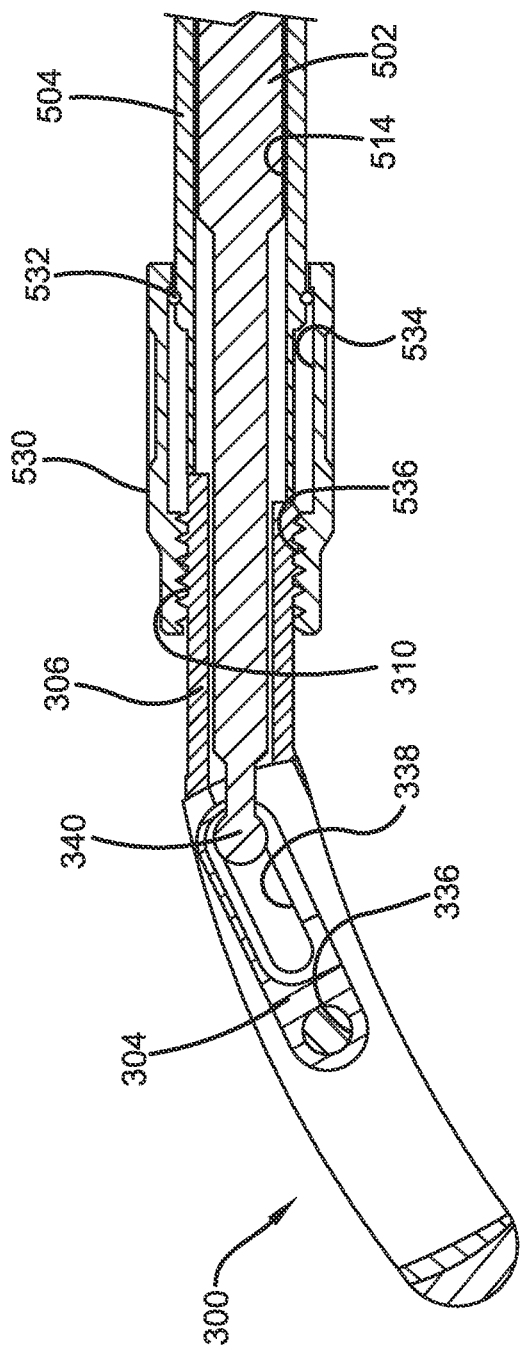
FIG. 26 is a close-up view of the distal end of the vertebral body shaver assembly shown in FIG. 23.

As shown in FIGS. 26-28, in some embodiments, the proximal end of the shaver housing 306 may have threads 310. Threads 310 may be, as shown, formed on a circular outer surface of the shaver housing 306. In some embodiments, with reference now to FIGS. 22, 24 and 26, to attach the housing 504 to the shaver instrument 300, a lock nut 530 and retainer ring 532 may be used. Lock nut 530 may have an opening 534 that extends along its longitudinal axis and a portion of the circumference of the opening 534 may include threads 536 designed to engage the threads 310 of the shaver housing 306. The housing 504 may have a circular indentation 538 on its outer surface sized and shaped to receive the retainer ring 532 and thereby attach the housing 306 to the lock nut 530 when the housing 306 is inserted within opening 534.

Figure 25:
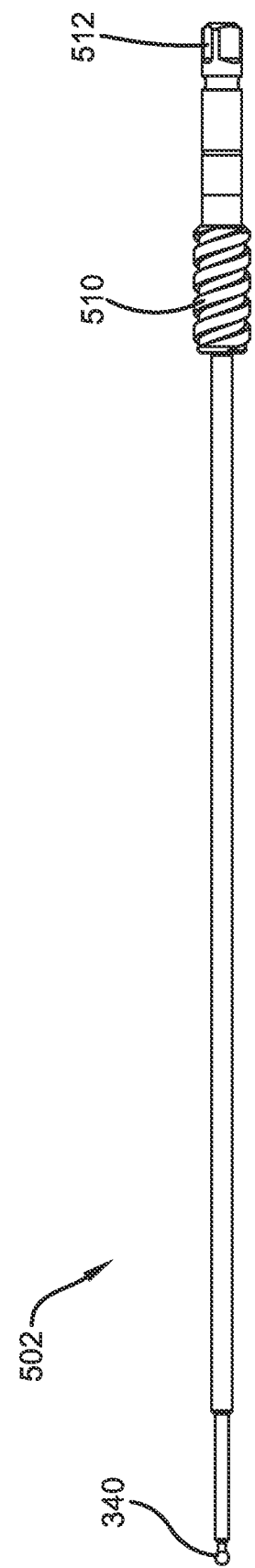
FIG. 25 is a side view of a shaft.

With reference now to FIGS. 22-23 and 25, in some embodiments, handle 506 may attach directly to the tool reception surface 512 of the shaft 502. In other embodiments, shown, a connector 540 may be used. The distal end of the connector 540 may attach to the tool reception surface 512 and the proximal end of the connector 540 may attach to the handle 506, as shown. The connector may provide for ease of assembly; namely a "quick connect" type attachment between the handle 506 and the shaft 502.

With reference now to FIGS. 22-28, operation of the shaver inserter 500 and shaver instrument 300 will now be described. First the appropriately sized shaver instrument 300 may be selected by the surgeon to match the spinal implant to be inserted. The shaver inserter 500 may then be assembled by positioning the shaft 502 within the housing 504 with threads 510 engaging threads 516. The insert member 340 may extend through the opening 362 in the shaver housing 306 and be positioned within the groove 338 in the hinge swivel 304. The proximal end of the lock nut 530 may then be attached to the distal end of the housing 504 (using the retainer ring 532 if desired) and the distal end of the lock nut 530 may be attached to the proximal end of the shaver housing 306 (such as by rotating the lock nut 530 about its longitudinal axis as threads 536 engage threads 310). Handle 506 may be attached to the shaft 502 as described above.

With reference now to FIGS. 1-2, 7 and 22-28, the surgeon may then insert the shaver instrument 300 in the contracted condition (FIG. 27) into the vertebral space 114, 212 using the shaver inserter 500. In some embodiments, shown, the shaver instrument is adapted to be inserted into the intradiscal space anterolaterally, posteriorly, or posterolaterally. Once the shaver instrument 300 is in the proper position, the surgeon may shave/cut vertebral material from the spinal endplates by causing the blade support device 302 to pivot around its pivot axis from the position shown in FIG. 27 to the position shown in FIG. 28. In some embodiments, shown, the pivot axis 324 remains perpendicular to the first and second vertebral body endplates during this pivoting motion. The surgeon may cause this pivoting motion by holding handle 506 with one hand and either handle 522 or grip surface 520 with the other hand and then rotating the housing 504 with respect to handle 506. This motion causes the shaft 502 to move distally causing the blade support device 302 to pivot as described above. When the surgeon rotates the housing 504 in the opposite direction, shaft 502 moves proximally causing the rotary blade to pivot in the opposite direction—back to the position shown in FIG. 27. These steps can be repeated until the desired shaving/cutting has been achieved. The shaver instrument 300 may then be; returned to the contracted condition (FIG. 27); removed from the vertebral space 114, 212; and then removed from the shaver inserter 500.

With reference now to FIGS. 1-21 and 27-28, operation of the shaver inserter 400 and shaver instrument 300 will now be described. First the appropriately sized shaver instrument 300 may be selected by the surgeon to match the spinal implant to be inserted. The shaver inserter 400 may then be assembled by positioning the shaft 402 within the housing 404. The insert member 340 may be positioned within the groove 338 in the hinge swivel 304. Handle 406 may be attached to the proximal end of the housing 404 by engaging handle 406 to the handle attachment surface 416 of the housing 404 and to the proximal end of the shaft 402 by engaging threads 410 with threads 432.

With reference now to FIGS. 1-2, 7 and 22-28, the surgeon may then insert the shaver instrument 300 in the contracted condition (FIG. 27) into the vertebral space 114, 212 using the shaver inserter 400. In some embodiments, shown, the shaver instrument is adapted to be inserted into the intradiscal space anterolaterally, posteriorly, or posterolaterally. Once the shaver instrument 300 is in the proper position, the surgeon may shave/cut vertebral material from the spinal endplates by causing the blade support device 302 to pivot around its pivot axis from the position shown in FIG. 27 to the position shown in FIG. 28. In some embodiments, shown, the pivot axis 324 remains perpendicular to the first and second vertebral body endplates during this pivoting motion. The surgeon may cause this pivoting motion by rotating the handle 406. This motion causes the shaft 402 to move distally causing the blade support device 302 to pivot as described above. When the surgeon rotates the handle 406 in the opposite direction, shaft 402 moves proximally causing the rotary blade to pivot in the opposite direction—back to the position shown in FIG. 27. These steps can be repeated until the desired shaving/cutting has been achieved. The shaver instrument 300 may then be; returned to the contracted condition (FIG. 27); removed from the vertebral space 114, 212; and then removed from the shaver inserter 400.

This expandable design is very beneficial for the surgeon. When in the non-deployed, contracted, reduced footprint condition, shaver instrument 300 is small enough to be passed through a standard microdiscectomy type annulotomy, making it truly compatible with minimally invasive surgical (MIS) techniques. Once placed within the vertebral space, the shaver instrument 300 may be adjusted into the expanded condition where it can be used for shaving/cutting. This larger footprint is compatible with more invasive anterior lumbar interbody fusion or bilateral posterior techniques.

I claim:

1. A vertebral body shaver assembly comprising:
   a shaver inserter including:
      1) an inserter housing having an opening;
      2) a shaft:
         (a) received in the opening in the inserter housing;
         (b) having proximal and distal ends; and
      3) a handle operatively engaged to the proximal end of the shaft; and
   a shaver instrument including:
      1) a shaver housing; and
      2) a blade support device:
         (a) that supports a first blade;
         (b) that is pivotal with respect to the shaver housing about a pivot axis; and
         (c) that is operatively engaged to the distal end of the shaft;
   wherein:
      1) the shaver inserter is adapted to insert the shaver instrument into an intradiscal space between first and second vertebral body endplates in a non-expanded condition where a first endplate facing surface of the shaver housing and a first endplate facing surface of the blade support device together define a first effective footprint area A1 with respect to the vertebral body endplates;
      2) after the shaver housing and the blade support device are properly positioned within the intradiscal space:
         (a) the handle is selectively operable to adjust the shaft to cause the blade support device to pivot about the pivot axis with respect to the shaver housing from the non-expanded condition to an expanded condition where the first endplate facing surface of the shaver housing and the first endplate facing surface of the blade support device together define a second effective footprint area A2 with respect to the vertebral body endplates; and
         (b) as the blade support device is selectively pivoted from the non-expanded condition to the expanded condition, the first blade is adapted to shave osteochondral material off the first vertebral body endplate; and
         (c) as the blade support device is selectively pivoted from the non-expanded condition to the expanded condition, the pivot axis remains perpendicular to the first and second vertebral body endplates; and
      3) the ratio A2/A1 is at least 1.05.

2. The vertebral body shaver assembly of claim 1 wherein:
   the inserter housing has proximal and distal ends;
   the distal end of the inserter housing operatively engages the shaver housing;
   the blade support device includes a groove having a length;
   the distal end of the shaft has an insert member that is received in the groove; and
   the handle is selectively operable to adjust the shaft to move the insert member along the length of the groove to cause the blade support device to pivot about the pivot axis with respect to the shaver housing from the non-expanded condition to the expanded condition.

3. The vertebral body shaver assembly of claim 2 wherein:
   the shaft has a longitudinal axis; and the handle is selectively rotatable to cause the shaft to rotate within the opening in the inserter housing and to move longitudinally within the opening in the inserter housing to move the insert member along the length of the groove to cause the blade support device to pivot about the pivot axis with respect to the shaver housing from the non-expanded condition to the expanded condition.

4. The vertebral body shaver assembly of claim 1 wherein:

the shaver instrument is adapted to be inserted into the intradiscal space anterolaterally, posteriorly, or posterolaterally.

5. The vertebral body shaver assembly of claim 1 wherein:

the blade support device has a longitudinal axis that is perpendicular to the pivot axis;

the first blade is positioned on a first longitudinal end of the blade support device and extends in a first linear direction;

the blade support device supports a second blade, distinct from the first blade, that is positioned on a second longitudinal end of the blade support device, opposite the first longitudinal end, and extends in a second linear direction, opposite the first direction;

the pivot axis is positioned longitudinally between the first and second longitudinal ends; and as the blade support device is selectively pivoted from the non-expanded condition to the expanded condition:
1) the first blade is adapted to shave osteochondral material off a first portion of the first vertebral body endplate; and
2) the second blade is adapted to shave osteochondral material off a second portion of the first vertebral body endplate, distinct from the first portion of the first vertebral body endplate.

6. The vertebral body shaver assembly of claim 5 wherein:

the blade support device supports a third blade, distinct from the first and second blades, that is positioned on the first longitudinal end of the blade support device and extends in the first linear direction;

the blade support device supports a fourth blade, distinct from the first, second and third blades, that is positioned on the second longitudinal end of the blade support device and extends in the second linear direction;

as the blade support device is selectively pivoted from the non-expanded condition to the expanded condition:
1) the third blade is adapted to shave osteochondral material off a first portion of the second vertebral body endplate; and
2) the fourth blade is adapted to shave osteochondral material off a second portion of the second vertebral body endplate, distinct from the first portion of the second vertebral body endplate.

7. The vertebral body shaver assembly of claim 6 wherein:

as the blade support device is selectively pivoted from the non-expanded condition to the expanded condition, the blade support device pivots about the pivot axis with respect to the shaver housing at least 45 degrees.

8. A vertebral body shaver instrument comprising:
a shaver housing; and
a blade support device:
1) that supports a first blade; and
2) that is pivotal with respect to the shaver housing about a pivot axis;
wherein:
1) the vertebral body shaver instrument is adapted to be inserted into an intradiscal space between first and second vertebral body endplates in a non-expanded condition where a first endplate facing surface of the shaver housing and a first endplate facing surface of the blade support device together define a first effective footprint area A1 with respect to the vertebral body endplates;
2) after the shaver housing and the blade support device are properly positioned within the intradiscal space:
(a) the blade support device is selectively pivotal about the pivot axis with respect to the shaver housing from the non-expanded condition to an expanded condition where the first endplate facing surface of the shaver housing and the first endplate facing surface of the blade support device together define a second effective footprint area A2 with respect to the vertebral body endplates;
(b) as the blade support device is selectively pivoted from the non-expanded condition to the expanded condition, the first blade is adapted to shave osteochondral material off the first vertebral body endplate; and
(c) as the blade support device is selectively pivoted from the non-expanded condition to the expanded condition, the pivot axis remains perpendicular to the first and second vertebral body endplates; and
3) the ratio A2/A1 is at least 1.05.

9. The vertebral body shaver instrument of claim 8 wherein:

the vertebral body shaver instrument is adapted to be inserted into the intradiscal space anterolaterally, posteriorly, or posterolaterally.

10. The vertebral body shaver instrument of claim 8 wherein:

the blade support device has a longitudinal axis that is perpendicular to the pivot axis;

the first blade is positioned on a first longitudinal end of the blade support device and extends in a first linear direction;

the blade support device supports a second blade, distinct from the first blade, that is positioned on a second longitudinal end of the blade support device, opposite the first longitudinal end, and extends in a second linear direction, opposite the first direction;

the pivot axis is positioned longitudinally between the first and second longitudinal ends; and as the blade support device is selectively pivoted from the non-expanded condition to the expanded condition:
1) the first blade is adapted to shave osteochondral material off a first portion of the first vertebral body endplate; and
2) the second blade is adapted to shave osteochondral material off a second portion of the first vertebral body endplate, distinct from the first portion of the first vertebral body endplate.

11. The vertebral body shaver instrument of claim 8 wherein:

the blade support device supports a second blade, distinct from the first blade; and as the blade support device is selectively pivoted from the non-expanded condition to the expanded condition, the second blade is adapted to shave osteochondral material off the second vertebral body endplate.

12. The vertebral body shaver instrument of claim 8 wherein:
the blade support device has a longitudinal axis that is perpendicular to the pivot axis;
the first blade:
1) is positioned on a first longitudinal end of the blade support device; and
2) extends in a first linear direction;
a second blade, distinct from the first blade:
1) is supported on the blade support device;
2) is positioned on a second longitudinal end of the blade support device, opposite the first longitudinal end; and
3) extends in a second linear direction, opposite the first direction;
a third blade, distinct from the first and second blades:
1) is supported on the blade support device;
2) is positioned on the first longitudinal end of the blade support device; and
3) extends in the first linear direction;
a fourth blade, distinct from the first, second and third blades:
1) is supported on the blade support device;
2) is positioned on the second longitudinal end of the blade support device; and
3) extends in the second linear direction;
as the blade support device is selectively pivoted from the non-expanded condition to the expanded condition:
1) the first blade is adapted to shave osteochondral material off a first portion of the first vertebral body endplate;
2) the second blade is adapted to shave osteochondral material off a second portion of the first vertebral body endplate, distinct from the first portion of the first vertebral body endplate;
3) the third blade is adapted to shave osteochondral material off a first portion of the second vertebral body endplate; and
2) the fourth blade is adapted to shave osteochondral material off a second portion of the second vertebral body endplate, distinct from the first portion of the second vertebral body endplate.

13. The vertebral body shaver instrument of claim 8 wherein:
the blade support device is selectively pivotal about the pivot axis with respect to the shaver housing at least 45 degrees from the non-expanded condition to the expanded condition.

14. The vertebral body shaver instrument of claim 13 wherein:
the blade support device is selectively pivotal about the pivot axis with respect to the shaver housing at least 85 degrees from the non-expanded condition to the expanded condition.

15. The vertebral body shaver instrument of claim 8 wherein:
the blade support device includes a groove having a length;
the groove is adapted to receive an insert member; and
the insert member is adapted, when moved within the groove along the length of the groove, to pivot the blade support device from the non-expanded condition to the expanded condition.

16. The vertebral body shaver instrument of claim 8 wherein:
the blade support device includes a concave surface juxtaposed to the first blade; and
the concave surface is adapted to receive and move osteochondral material that is shaved off the first vertebral body endplate by the first blade.

17. A vertebral body shaver method comprising the steps of:
A) providing a shaver inserter including:
1) an inserter housing having an opening;
2) a shaft:
(a) received in the opening in the inserter housing;
(b) having proximal and distal ends; and
3) a handle operatively engaged to the proximal end of the shaft;
B) providing a shaver instrument including:
1) a shaver housing; and
2) a blade support device:
(a) that supports a first blade;
(b) that is pivotal with respect to the shaver housing about a pivot axis; and
(c) that is operatively engaged to the distal end of the shaft;
C) providing the shaver inserter to be operable to insert the shaver instrument anterolaterally, posteriorly, or posterolaterally into an intradiscal space between first and second vertebral body endplates in a non-expanded condition where a first endplate facing surface of the shaver housing and a first endplate facing surface of the blade support device together define a first effective footprint area A1 with respect to the vertebral body endplates;
D) providing the handle, after the shaver housing and the blade support device are properly positioned within the intradiscal space, to be operable to adjust the shaft to cause the blade support device to pivot about the pivot axis with respect to the shaver housing from the non-expanded condition to an expanded condition where the first endplate facing surface of the shaver housing and the first endplate facing surface of the blade support device together define a second effective footprint area A2 with respect to the vertebral body endplates; and
wherein:
1) the ratio A2/A1 is at least 1.05; and
2) step D includes the steps of:
(a) providing the first blade to be operable to shave osteochondral material off the first vertebral body endplate; and
(b) maintaining the pivot axis in an orientation perpendicular to the first and second vertebral body endplates.

18. The vertebral body shaver method of claim 17 wherein:
step A includes the steps of:
1) providing the inserter housing with proximal and distal ends;
2) providing the shaft with a longitudinal axis; and
3) providing the distal end of the shaft with an insert member;
step B includes the steps of:
1) providing the blade support device with a groove having a length;
2) operatively engaging the distal end of the inserter housing with the shaver housing; and
3) positioning the insert member within the groove; and
step D includes the step of providing the handle to be selectively rotatable to:
1) rotate the shaft within the opening in the inserter housing;

2) move the shaft longitudinally within the opening in the inserter housing; and
3) move the insert member along the length of the groove to pivot the blade support device about the pivot axis with respect to the shaver housing from the non-expanded condition to the expanded condition.

19. The vertebral body shaver method of claim 18 wherein:
step B includes the steps of:
1) providing the blade support device with a longitudinal axis that is perpendicular to the pivot axis;
2) providing the first blade on a first longitudinal end of the blade support device and extending it in a first linear direction;
3) providing the blade support device with a second blade, distinct from the first blade, that is positioned on a second longitudinal end of the blade support device, opposite the first longitudinal end, and extending in a second linear direction, opposite the first direction;
4) providing the blade support device with a third blade, distinct from the first and second blades, that is positioned on the first longitudinal end of the blade support device and extending in the first linear direction;
5) providing the blade support device with a fourth blade, distinct from the first, second and third blades, that is positioned on the second longitudinal end of the blade support device and extending in the second linear direction; and
6) providing the pivot axis to be positioned longitudinally between the first and second longitudinal ends; and step D includes the steps of:
1) providing the first blade to be operable to shave osteochondral material off a first portion of the first vertebral body endplate;
2) providing the second blade to be operable to shave osteochondral material off a second portion of the first vertebral body endplate, distinct from the first portion of the first vertebral body endplate;
3) providing the third blade to be operable to shave osteochondral material off a first portion of the second vertebral body endplate; and
4) providing the fourth blade to be operable to shave osteochondral material off a second portion of the second vertebral body endplate, distinct from the first portion of the second vertebral body endplate.

20. The vertebral body shaver method of claim 19 wherein:
step D includes the step of: providing the blade support device to pivot about the pivot axis with respect to the shaver housing at least 45 degrees from the non-expanded condition to the expanded condition.

* * * * *